United States Patent [19]
Yamada et al.

[11] Patent Number: 5,146,002
[45] Date of Patent: Sep. 8, 1992

[54] AROYL KETONE DERIVATIVE, UV RAY ABSORBER COMPRISING THE SAME, AND COSMETIC COMPOSITION CONTAINING THE SAME

[75] Inventors: Shinji Yamada, Ichikai; Akira Kawamata, Utsunomiya; Genji Imokawa, Utsunomiya; Shinichi Masuda, Utsunomiya; Masakazu Yamaguchi; Koichi Niinaka, both of Ichikai; Hiroko Joukura, Utsunomiya, all of Japan

[73] Assignee: Kao Corporation, Tokyo, Japan

[21] Appl. No.: 577,567

[22] Filed: Sep. 5, 1990

[30] Foreign Application Priority Data

Sep. 5, 1989 [JP] Japan ................................ 1-229708
Jan. 22, 1990 [JP] Japan ................................ 2-12196

[51] Int. Cl.$^5$ ............................................. C07C 49/225
[52] U.S. Cl. ..................................... 568/337; 424/59
[58] Field of Search .................... 568/337, 335; 424/59

[56] References Cited

U.S. PATENT DOCUMENTS

| | | | |
|---|---|---|---|
| 3,082,071 | 3/1963 | Hartle et al. | 568/335 |
| 3,629,336 | 12/1971 | Idelson | 568/337 |
| 4,024,272 | 8/1975 | Rogalski et al. | 514/432 |
| 4,065,502 | 12/1977 | MacKay et al. | 568/335 |
| 4,082,807 | 4/1978 | Eiglmeier | 568/337 |
| 4,489,057 | 12/1984 | Welters et al. | 424/59 |
| 4,814,162 | 3/1989 | Lang et al. | 568/337 |

FOREIGN PATENT DOCUMENTS 2918775 11/1980 Fed. Rep. of Germany ...... 568/335

OTHER PUBLICATIONS

Sosnovskikh et al., Zh. Org. Khin, vol. 22, pp. 883-884 (1986).
Uhlemann et al., J. Prokt. Chem., vol. 315, pp. 31-38 (1973).
Kwialkowski et al., Trans. Metal Chem. vol. 3, pp. 305-308 (1978).
Nigani et al., Chem. Abst., vol. 98, # 143060d (1983).
Keller et al., Chem. Abst., vol. 97, # 150,723e (1984).

Primary Examiner—James H. Reamer
Attorney, Agent, or Firm—Oblon, Spivak, McClelland, Maier & Neustadt

[57] ABSTRACT

A novel aroyl ketone derivative represented by formula (I) is disclosed:

$$Ar(COCH_2COR^1)_n \qquad (I)$$

wherein $R^1$ represents a saturated or unsaturated hydrocarbon group having 1-24 carbon atoms, or a linear or branched alkoxyalkyl or alkenyloxyalkyl group having 1-24 carbon atoms, dialkylamino group having 1-24 carbon atoms, Ar represents a benzene or naphthalene ring which may be substituted with one or more hydroxyl groups, alkoxy groups having 1-24 carbon atoms, alkenyloxy groups having 1-24 carbon atoms, polyoxyleneoxy groups, or α-methylenedioxy groups, and n denotes an integer of 1-4. An UV-ray absorber and cosmetic composition comprising the aroyl ketone derivative of formula (I) are also disclosed. Aroyl ketone derivative (I) of the present invention can provide an excellent UV-ray absorbing effect and has outstanding stability against light, and the UV-ray absorber or cosmetic composition containing the aroyl ketone derivative (I) can exhibit an excellent sunscreening effect.

3 Claims, No Drawings

AROYL KETONE DERIVATIVE, UV RAY ABSORBER COMPRISING THE SAME, AND COSMETIC COMPOSITION CONTAINING THE SAME

BACKGROUND OF THE INVENTION

1. Field of the Invention

This invention relates to a novel aroyl ketone derivative possessing UV-ray absorbing ability and outstanding stability against light, and to a UV-ray absorber and a cosmetic composition both containing such an aroyl ketone derivative and exhibiting a superior effect of protecting the skin from sunburn.

2. Description of the Background Art

Ultraviolet rays are known to cause various changes to the skin. In dermatology, UV-rays are classified into (a) long wavelength UV-rays of 400–320 nm, (b) medium wavelength UV-rays of 320–290 nm, and (c) short wavelength UV-rays of less than 290 nm. These are called UV-A, UV-B, and UV-C, respectively. The UV-rays contained in the sunlight are UV-A and UV-B, whereas UV-C is absorbed in the ozone layer and therefore scarcely reaches the ground.

The UV-B, when irradiated onto the skin in an amount exceeding a certain level, causes red spots or blisters on the skin. In addition, the UV-B tends to promote the formation of melanin, resulting in the melanoses or other adverse changes of the skin. On the other hand, UV-A induces melanism on the skin immediately after irradiation (instantaneous melanism). In addition, UV-A energy reaches the corium and brings about chronic changes in the blood vessel walls and the elastic fibers in connective tissues. Such behaviors of both UV-A and UV-B are considered to accelerate aging of the skin and to be a cause of wrinkles, spots or freckles.

As such effects of UV-rays on human skin have been clarified, various chemical compounds capable of absorbing UV-A and/or UV-B have been developed. Such UV-ray absorbers are desired to satisfy the following requirements (1) through (5);

(1) absorbing UV-A or UV-B light to the maximum.
(2) having good stability against heat and light.
(3) being free from toxicity, irritation, and any other harmful actions to the skin.
(4) having a long-lasting effect.
(5) having an excellent compatibility with cosmetic base materials.

Conventionally, for example, dibenzoylmethane derivatives are used as a UV-A absorber; and derivatives of cinnamate, benzophenone, p-aminobenzoic acid, salicylic acid, and the like are used as a UV-B absorber.

However, these conventional UV-ray absorbers can not necessarily satisfy the above requirements. Specifically, these UV-ray absorbers are known to be inadequate in the stability against light and to decompose or react by UV-ray irradiation (Int. J. Cosmetic Science, 10, 53, 1988). Such decomposition of UV-ray absorbers substantially decreases the lasting effect of compositions. Adverse effects to the skin resulting from decomposed substances themselves or compounds produced by the reaction of the decomposed substances and other components can not be neglected (Fragrance Journal, 84, 34, 1987).

Development of improved UV-ray absorbers which satisfy the above characteristics, especially UV-ray absorbers having excellent stability against light, has therefore been desired.

The inventors have synthesized many diketone derivatives and examined their characteristics, and, as a result, found that an aroyl ketone derivative represented by formula (I) shown below had an outstanding UV-A and UV-B absorbing ability and excellent stability against light, and further found that a cosmetic composition comprising the aroyl ketone derivative could efficiently protect the skin from being sunburnt.

SUMMARY OF THE INVENTION

Accordingly, an object of this invention is to provide a novel aroyl ketone derivative represented by the following formula (I):

$$Ar(COCH_2COR^1)_n \qquad (I)$$

wherein $R^1$ represents a saturated or unsaturated hydrocarbon group having 1–24 carbon atoms, or a linear or branched alkoxyalkyl or alkenyloxyalkyl group having 1–24 carbon atoms, dialkylamino group having 1–24 carbon atoms, Ar represents a benzene or naphthalene ring which may be substituted with one or more hydroxyl groups, alkoxy groups having 1–24 carbon atoms, alkenyloxy groups having 1–24 carbon atoms; or α-methylenedioxy groups, and n denotes an integer of 1–4; excluding the compounds represented by the following formulae:

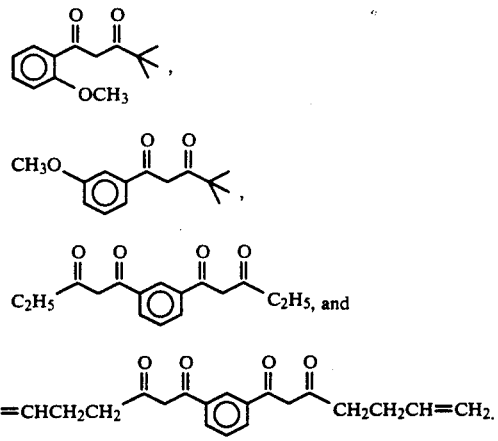

Another object of the present invention is to provide a UV-ray absorber comprising an aroyl ketone derivative represented by the following formula (I):

$$Ar(COCH_2COR^1)_n \qquad (I)$$

wherein $R^1$ represents a saturated or unsaturated hydrocarbon group having 1–24 carbon atoms, or a linear or branched alkoxyalkyl or alkenyloxyalkyl group having 1–24 carbon atoms, dialkylamino group having 1–24 carbon atoms, Ar represents a benzene or naphthalene ring which may be substituted with one or more hydroxyl groups, alkoxy groups having 1–24 carbon atoms, alkenyloxy groups having 1–24 carbon atoms, or α-methylenedioxy groups, and n denotes an integer of 1–4.

Still another object of this invention is to provide a cosmetic composition comprising an aroyl ketone derivative represented by the following formula (I):

$$Ar(COCH_2COR^1)_n \quad (I)$$

wherein $R^1$ represents a saturated or unsaturated hydrocarbon group having 1-24 carbon atoms, or a linear or branched alkoxyalkyl or alkenyloxyalkyl group having 1-24 carbon atoms, Ar represents a benzene or naphthalene ring which may be substituted with one or more hydroxyl groups, alkoxy groups having 1-24 carbon atoms, alkenyloxy groups having 1-24 carbon atoms, or α-methylenedioxy groups, and n denotes an integer of 1-4.

Other objects, features and advantages of the invention will hereinafter become more readily apparent from the following description.

DETAILED DESCRIPTION OF THE INVENTION AND PREFERRED EMBODIMENTS

Enumerated as examples of $R^1$ having 1-24 carbon atoms, saturated or unsaturated, are methyl, ethyl, n-propyl, isopropyl, n-butyl, isobutyl, t-butyl, butenyl, n-pentyl, n-hexyl, n-heptyl, heptenyl, n-octyl, octenyl, n-nonyl, nonenyl, n-decyl, decenyl, n-undecyl, undecenyl, n-dodecyl, dodecenyl, n-tridecyl, tridecenyl, n-tetradecyl, tetradecenyl, n-pentadecyl, pentadecenyl, isopentadecyl, n-hexadecyl, hexadecenyl, isohexadecyl, n-heptadecyl, heptadecenyl, isoheptadecyl, n-octadecyl, octadecenyl, isooctadecyl, cyclohexyl, and adamantyl groups and the like. Enumerated as examples of hydroxyalkyl groups having 1-18 carbon atoms are hydroxymethyl, hydroxyethyl, hydroxypropyl, hydroxybutyl, hydroxypentyl, hydroxyhexyl, hydroxyheptyl, hydroxyoctyl, hydroxynonyl, hydroxydecyl, hydroxyundecyl, hydroxydodecyl, hydroxytetradecyl, hydroxyhexadecyl, hydroxyoctadecyl groups and the like. Enumerated as examples of linear or branched alkoxyalkyl groups having 1-24 carbon atoms are methoxymethyl, ethoxymethyl, propoxymethyl, isopropoxymethyl, butoxymethyl, pentyloxymethyl, hexyloxymethyl, octyloxymethyl, decyloxymethyl, undecyloxymethyl, tetradecyloxymethyl, hexadecyloxymethyl, octadecyloxymethyl, methoxyethyl, ethoxyethyl, allyloxyethyl, propoxyethyl, methoxypropyl, ethoxypropyl, allyloxypropyl, propoxypropyl, methoxybutyl, ethoxybutyl, allyloxybutyl, propoxybutyl, methoxypentyl, ethoxypentyl, allyloxypentyl, propoxypentyl, methoxydodecyl, ethoxydodecyl, allyloxyiodecyl, propoxydodecyl, methoxyhexadecyl, ethoxyhexadecyl, allyloxyhexadecyl, propoxyhexadecyl, methoxyhexadecyl, ethoxyoctadecyl, allyloxyoctadecyl, propoxyoctadecyl groups, and the like. Given as examples of alkenyloxyalkyl groups having 1-24 carbon atoms are allyloxymethyl, butenyloxymethyl, hexenyloxymethyl, undecenyloxymethyl, octadecenyloxymethyl groups, and the like. Enumerated as examples of dialkylamino groups having 1-24 carbon atoms are dimethylamino, ethylmethylamino, diethylamino, methylpropylamino, methylisopropylamino, methylbutylamino, methyl-t-butylamino, diisopropylamino, dipropylamino, ethylbutylamino, methylhexylamino, di-sec-butylamino, diisobutylamino, dipentylamino, dihexylamino, bis 2-ethylhexylamino, dioctylamino, methyloctadecylamino, pyrrolidyl, piperidyl, morpholinyl groups, and the like. Preferable examples of linear or branched alkoxy groups having 1-24 carbon atoms, by which the benzene or naphthalene ring (Ar) may be substituted, are those having 1-8 carbon atoms, for example, methoxy, ethoxy, n-propoxy, isopropoxy, n-butoxy, and tert-butoxy groups, and the like. Preferable examples of alkenyloxy groups having 1-24 carbon atoms, by which the benzene or naphthalene ring (Ar) may be substituted, are those having 1-8 carbon atoms, for example, allyloxy, butenyloxy, pentenyloxy and hexenyloxy groups, and the like. n is an integer of 1-4, but its preferable range is 1-3.

Aroyl ketone derivative (I) of the present invention can be produced by one of the following processes (a), (b) or (C), according to known methods, for example, reported in J. Am. Chem. Soc., 80, 4891, (1958); J. Chromatogr., 312, 109, (1984); and J. Polym. Sci. Polym. Chem. Ed., 20, 3079, (1982).

Process (a):

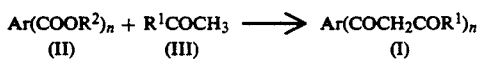

$$Ar(COOR^2)_n + R^1COCH_3 \longrightarrow Ar(COCH_2COR^1)_n$$
$$\text{(II)} \qquad \text{(III)} \qquad \text{(I)}$$

wherein $R^2$ represents a methyl group, ethyl group, n-propyl group, or a n-butyl group and $R^1$ and n have the same meanings as defined above.

As is clear from the above reaction scheme, compound (I) of the present invention can be prepared by condensation of an ester of formula (II) and a ketone of formula (III). In process (a), it is desirable that the reaction be carried out at 20°-150° C. for tens of minutes to 10 hours in a solvent such as anhydrous tetrahydrofuran, toluene, xylene, or the like using a base as a catalyst. The base used in this process is a metallic hydride, e.g. sodium hydride; an alkyl metal, e.g. butyl lithium; an amine, e.g. triethylamine; a metal amide, e.g. sodium amide; a metal alkoxyde, e.g. sodium methoxide; and the like.

Process (b):

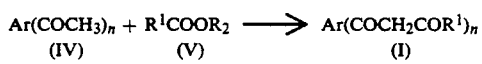

$$Ar(COCH_3)_n + R^1COOR_2 \longrightarrow Ar(COCH_2COR^1)_n$$
$$\text{(IV)} \qquad \text{(V)} \qquad \text{(I)}$$

wherein $R^1$, $R^2$, and n have the same meanings as defined above.

As is clear from the above reaction scheme, compound (I) of the present invention can be prepared by condensation of an acetylbenzene derivative or an acetylnaphthalene derivative of formula (IV) and an ester of formula (V). The reaction of process (b) can be carried out under the same conditions as in process (a).

Process (c):

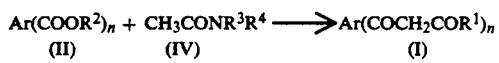

$$Ar(COOR^2)_n + CH_3CONR^3R^4 \longrightarrow Ar(COCH_2COR^1)_n$$
$$\text{(II)} \qquad \text{(IV)} \qquad \text{(I)}$$

wherein $R^1$, $R^2$, and n have the same meanings as defined above. $R^3$ and $R^4$ each represents a hydrocarbon group having 1-18 carbon atoms, which may form a ring such as,

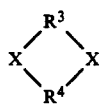

wherein X is oxygen.

As is clear from the above reaction scheme, compound (I) of the present invention can be prepared by condensation of an ester of formula (II) and an acetoamide of formula (IV). The reaction of process (c) can be carried out under the same conditions as in process (a).

The UV-ray absorbing agent of the present invention may consist of one or more aroyl ketone derivatives of formula (I) thus obtained. However, it is more desirable to use the aroyl ketone derivatives of the present invention mixed with a carrier. Any kind of carriers which are inert to the aroyl ketone derivative (I) of the present invention and in the form either of solid, liquid, emulsion, foam, gel, or the like can be used. Typical examples of these carriers are water; alcohols; oil and fats, e.g. hydrocarbon oils, fatty acid esters, long-chain alcohols, silicone; micro powders of starch, talc, and the like; low boiling point hydrocarbons or halogenated hydrocarbons used as an conventional aerosol propellant; and the like. In addition to the above components, any conventional components may be incorporated in the UV-ray absorber of the present invention to the extent that the UV-ray absorbing effect of the aroyl ketone derivative of the present invention will not be impaired. These conventional components include, for example, antiseptics, perfumes, pigments, surfactants, and the like.

The cosmetic compositions containing the aroyl ketone derivative (I) of the present invention (hereinafter designated as "cosmetic composition of the present invention") can be produced by incorporating one or more aroyl ketone derivatives (I) having compatibility with the base components of the cosmetic composition according to a conventional method. The cosmetic composition can be prepared into various forms such as creams, liquids, oils, sprays, sticks, emulsions, foundations, ointments, and the like.

The selective use of aroyl ketone derivatives (I) which are compatible with the cosmetic bases ensures preparation of cosmetic compositions having UV-ray absorbing effect of various types, for example, fundamental cosmetics such as cosmetic oils with oil bases, oil creams and milky lotions with a large quantity of oil, weakly oily creams and lotions, water-base lotions; and make-up cosmetics such as oil-base foundations, lipsticks. Examples of these base components or solvents useful for the cosmetic compositions of the present invention are hydrocarbons such as solid or liquid paraffins, crystal oils, ceresin, ozokerite, montan wax, and the like; oils, fats, or waxes of plant or animal origin such as olive oil, earth wax, carnauba wax, lanolin, spermaceti, and the like; fatty acids and esters thereof such as stearic acid, palmitic acid, oleic acid, glycerol monostearate, glycerol distearate, glycerol monooleate, isopropyl myristate, isopropyl stearate, butyl stearate, and the like; alcohols such as ethyl alcohol, isopropyl alcohol, cetyl alcohol, stearyl alcohol, palmityl alcohol, hexyldodecyl alcohol, and the like. In addition, polyhydric alcohols having a moisturizing effect such as glycol, glycerol, sorbitol, and the like may also be used.

The amount of aroyl ketone derivative (I) to be incorporated in the UV-ray absorbing agent or cosmetic composition of the present invention varies depending on their types or forms of products. There are no specific limitations as to the amount to be added in inasmuch as such an addition brings about the effect of the present invention. A preferable amount is 0.1-20% by weight, and particularly 0.5-10% by weight, of the crude product.

The UV-ray absorbing agent or cosmetic composition of the present invention can be prepared by simply incorporating the aroyl ketone derivative (I) as a UV-ray absorber. However, it is more preferable to provide a sunscreen cosmetics for general use by incorporating conventional UV-A or UV-B absorbers together with the aroyl ketone derivative (I) of this invention. Examples of these conventional UV-B absorbers include, p-methylbenzylidene-D,L-camphor or its sodium sulfonate, sodium 2-phenylbenzimidazole-5-sulfonate, sodium 3,4-dimethylphenylglyoxylate, 4-phenylbenzophenone, isooctyl 4-phenylbenzophenone-2,-carboxylate, p-methoxycinnamate, 2-phenyl-5-methylbenzoxazol, p-dimethylaminobenzoate, and the like. Examples of the UV-A absorbers are 4-methoxy-2'-carboxydibenzoylmethane, 4-methoxy-4'-t-butyldibenzoylmethane, 4-isopropyldibenzoylmethane, 2-hydroxy-4-methoxybenzophenone, dibenzylidenecamphor, and the like.

Into the cosmetic compositions of the present invention, various additives other than the above-mentioned components can be incorporated. Suitable additives are, for example, W/O and O/W emulsifiers which are available in the market; and viscosity increasing agents such as methyl-, ethyl-, or carboxymethyl cellulose, polyacrylic acid, tragacanth, agar, gelatin, and the like. As required, perfumes, antiseptics, humectants, emulsion stabilizers, medical components, and/or coloring agents which ar physiologically acceptable, may also be formulated into the cosmetic composition of this invention.

Other features of the invention will become apparent in the course of the following description of the exemplary embodiments which are given for illustration of the invention and are not intended to be limiting thereof.

EXAMPLES

Example 1

Synthesis of 3,4-dimethoxy(4,4-dimethyl-3-oxopentanoyl)benzene

In a 200 ml three-necked flask equipped with a mechanical stirrer, dropping funnel, reflux condenser, and a nitogen-inlet tube, 2.45 gm (61 mmol) of 60% sodium hydride, 10 gm (51 mmol) of methyl 3,4-dimethoxybenzoate, and 100 ml of anhydrous tetrahydrofuran were mixed with stirring under nitrogen stream, and refluxed with heating while 6.1 gm (61 mmol) of pinacolone was added dropwise. The refluxing under heat was continued for 7 hours. After cooling the reaction mixture, 30 ml of 2N hydrochloric acid was added and the mixture was extracted twice with chloroform. The extract was dried over anhydrous sodium sulfate and the solvent was removed by evaporation to give a crude product. Hexane was added to the crude product and insoluble substances were filtered off. The filtrate was concentrated by evaporation, and recrystallization afforded 8.9 gm of the target compound as colorless needles (yield: 65%).

Melting Point: 52.3°–53.3° C.

IR($\gamma KBr$, cm$^{-1}$): 1602, 1521, 1470, 1446, 1365, 1299, 1266, 1218, 1188, 1131, 885, 786, 729.

$^1$H-NMR(CDCl$_3$, δ): 1.26(9 H, s, t-C$_4$H$_9$), 3.95(3 H, s, OCH$_3$), 3.96(3 H, s, OCH$_3$), 6.24(1 H, s), 6.90(1 H, d, J=8.4 Hz), 7.49(1 H, s), 7.51(1 H, d, J=8.4 Hz).

Elemental analysis: Calculated (%) C: 68.16, H: 7.63; Found (%) C: 68.23, H: 7.60.

Example 2

Synthesis of 3,4,5-trimethoxy(4,4-dimethyl-3-oxopentanoyl)benzene

In a 200 ml three-necked flask equipped with a mechanical stirrer, dropping funnel, reflux condenser, and a nitogen-inlet tube, 3.0 gm (75 mmol) of 60% sodium hydride, 10 gm (44.3 mmol) of methyl 3,4,5-oxopentanoyl)benzene trimethoxybenzoate, and 80 ml of anhydrous tetrahydrofuran were mixed with stirring under nitrogen stream, and refluxed with heating while 5.3 gm (53.2 mmol) of pinacolone was added dropwise. Refluxing under heat was continued for 5 hours. After cooling the reaction mixture, 45 ml of 2N hydrochloric acid was added, the mixture was extracted twice with chloroform. The extract was dried over anhydrous sodium sulfate and the solvent was removed by evaporation to give a crude product. Hexane was added to the crude product and insoluble substances were filtered off. The filtrate was concentrated by evaporation, and recrystallization afforded 9.6 gm of the target compound as colorless needles (yield: 74%).

Melting Point: 67.3°–68.4° C.

$IR(\gamma_{KBr}, cm^{-1})$: 2968, 1593, 1560, 1509, 1473, 1434, 1335, 1233, 1218, 1176, 1131, 993, 801.

$^1$H-NMR(CDCl$_3$, δ): 1.26(9 H, s, t-C$_4$H$_9$), 3.91(3 H, s, OCH$_3$), 3.93(6 H, s, OCH$_3$), 6.21(1 H, s), 7.13(2 H, s).

Elemental analysis: Calculated (%) C: 65.29, H: 7.53; Found (%) C: 65.38, H: 7.51.

Example 3

Synthesis of 1,4-bis(4,4-dimethyl-3-oxopentanoyl)benzene

In a 2 l four-necked flask equipped with a mechanical stirrer, dropping funnel, thermometer, reflux condenser, and a nitrogen-inlet tube, 32 gm (0.8 mol) of 60% sodium hydride, 79 gm (0.79 mol) of pinacolone, and 700 ml of anhydrous tetrahydrofuran were mixed with stirring under nitrogen stream. To this solution, 70 gm (0.36 mol) of dimethylterephthalate in 300 ml of tetrahydrofuran was added dropwise over one hour. After the addition, the reaction mixture was refluxed with heating for 6 hours, and was cooled to room temperature. After addition of 180 ml of 2N aqueous hydrochloric acid, the reaction mixture was extracted with chloroform. The extract was dried over anhydrous sodium sulfate and the solvent was evaporated to give a crude product. The crude product was recrystallized using hexane to obtain 78 gm of the target compound as colorless scales (yield: 66%).

Melting Point: 125.5°–126.5° C.

$IR(\gamma_{KBr}, cm^{-1})$: 2974, 2872, 1584, 1563, 1485, 1368, 1290, 1140, 840, 792, 741.

$^1$H-NMR(CDCl$_3$, δ): 1.27(18 H, s), 6.34(2 H, s), 7.95(4H, s).

Elemental analysis: Calculated (%) C: 72.70, H: 7.93; Found (%) C: 72.61, H: 7.96.

Example 4

Synthesis of 1,3-bis(4,4-dimethyl-3-oxopentanoyl)benzene

In a 100 ml three-necked flask equipped with a mechanical stirrer, dropping funnel, reflux condenser, and a nitogen-inlet tube, 1.5 gm (38 mmol) of 60% sodium hydride, 3.6 gm (36 mmol) of pinacolone, 3.0 gm (15.5 mmol) of dimethyl isophthalate, and 30 ml of anhydrous tetrahydrofuran were mixed with stirring under nitrogen stream and refluxed with heating for 6 hours. After cooling the reaction mixture, 10 ml of 2N aqueous hydrochloric acid was added the product was extracted with chloroform. The extract was dried over anhydrous sodium sulfate and the solvent was evaporated to give a crude product. Recrystallization using hexane afforded 3.1 gm of the target compound as colorless crystals (yield: 61%).

Melting Point: 106.0°–107.5° C.

$IR(\gamma_{KBr}, cm^{-1})$: 3124, 2974, 2872, 1611, 1563, 1482, 1431, 1290, 1227, 1134, 1095, 879, 804, 705.

$^1$H-NMR(CDCl$_3$, δ): 1.27(18 H, br.s), 6.34(2 H, s), 7.55(1 H, br.t, J=7.8 Hz), 8.00 and 8.04(2 H, dd, J=7.8 Hz, J=1.5 Hz), 8.38(1 H, br.s).

Elemental analysis: Calculated (%) C: 72.70, H: 7.93; Found (%) C: 72.58, H: 7.95.

Example 5

Synthesis of 4-methoxy-1,3-bis(4,4-dimethyl-3-oxopentanoyl)benzene

In a 100 ml three-necked flask equipped with a mechanical stirrer, dropping funnel, reflux condenser, and a nitogen-inlet tube, 1.5 gm (38 mmol) of 60% sodium hydride, 3.6 gm (36 mmol) of pinacolone, 3.0 gm (13.4 mmol) of dimethyl 4-methoxyisophthalate, and 30 ml of anhydrous tetrahydrofuran were mixed with stirring under nitrogen stream and refluxed with heating for 5 hours. After cooling the reaction mixture, 10 ml of 2N aqueous hydrochloric acid was added, and the product was extracted with chloroform. The extract was dried over anhydrous sodium sulfate and the solvent was removed by evaporation. The crude product was recrystallized using hexane to obtain 3.2 gm of the target compound as colorless crystals (yield: 66%).

Melting Point: 69.4°–70.8° C.

$IR(\gamma_{KBr}, cm^{-1})$: 2968, 1620, 1584, 1506, 1467, 1368, 1275, 1263, 1182, 1131, 1071, 1011, 795.

$^1$H-NMR(CDCl$_3$, δ): 1.24(9 H, s), 1.25(9 H, s), 3.99(3 H, s), 6.29(1 H, s), 6.52(1 H, s), 7.04(1 H, d, J=8.8 Hz), 8.04(1 H, dd, J=2.3 Hz, J=8.8 Hz), 8 35(1 H, d, J=2.3 Hz).

Elemental analysis: Calculated (%) C: 69.98, H: 7.83; Found (%) C: 69.92, H: 7.85.

Example 6

Synthesis of 2,6-bis(4,4-dimethyl-3-oxopentanoyl)-naphthalene

To 2.0 gm of dimethyl 2,6-naphthalene dicarboxylate and 2.8 gm of pinacolone, which had been dissolved in 25 ml of anhydrous tetrahydrofuran, 1.1 gm of 60% sodium hydride was added. The mixture was reacted at 60° C. for 4 hours while stirring. The reaction mixture was poured into ice-cooled 2N hydrochloric acid. Organic substances were extracted using chloroform and, after evaporating the solvent, recrystallized in a mixed solvent of chloroform-methanol to obtain 2.1 gm of the target compound as pale yellow crystals.

Melting Point: 195°–196° C.

$IR(\gamma_{KBr}, cm^{-1})$: 2968, 2936, 2872, 1618, 1580, 1512, 1480, 1430, 1182, 1154, 1128, 1070, 1018, 910, 812, 710, 474.

$^1$H-NMR(CDCl$_3$, δ): 15.81(2 H, s), 8.62(2 H, s), 7.94–8.10(4 H, m), 6.47(2 H, s), 1.30(18 H, s).

Example 7

Synthesis of 1,4-bis(4-methyl-3-oxopentanoyl)-benzene

The procedures in Example 3 were repeated under substantially same conditions except that 68 gm (0.79 mol) of isopropylmethylketone was used instead of 79 gm (0.79 mol) of pinacolone, and afforded 76 gm of the target compound as pale yellow needles (Yield: 72%).

Melting Point: 97.0°–97.5° C.

IR($\gamma_{KBr}$, cm$^{-1}$): 2980, 2932, 1608, 1437, 1284, 1188, 1098, 939, 807.

$^1$H-NMR(CDCl$_3$, δ): 1.25(12 H, d), 2.55–2.77(2 H, m), 6.25(2 H, s), 7.95(4 H, s), 14.7(2 H, bs).

Example 8

Synthesis of 1,4-bis(3-oxopentanoyl)benzene

The procedures in Example 3 were repeated under substantially same conditions except that 57 gm (0.79 mol) of methylethylketone was used instead of 79 gm (0.79 mol) of pinacolone, and afforded 54 gm of the target compound as pale yellow crystals (Yield: 56%).

Melting Point: 122.5°–123.5° C.

IR($\gamma_{KBr}$, cm$^{-1}$): 2980, 2950, 1617, 1293, 1161, 1119, 1083, 813, 774.

$^1$H-NMR(CDCl$_3$, δ): 1.25(6 H, t), 2.50(4 H,q), 6.22(2 H, s), 7.95(4 H, s), 15.2(2 H, bs).

Example 9

Synthesis of 1,4-bis(3-oxododecanoyl)benzene

In a 100 ml three-necked flask equipped with a mechanical stirrer, dropping funnel, reflux condenser, and a nitrogen-inlet tube, 1.1 gm (28 mmol) of 60% sodium hydride, 2.0 gm (12.3 mmol) of p-diacetylbenzene, 4.8 gm (25.7 mmol) of methylcaprylate, and 20 ml of anhydrous tetrahydrofuran were mixed with stirring under nitrogen stream and the refluxing under heat was continued for 5 hours. After cooling the the reaction mixture, 15 ml of 2N aqueous hydrochloric acid was added, and the mixture was extracted with chloroform. The extract was dried over anhydrous sodium sulfate and the solvent was removed by evaporation to give a crude product. Hexane was added to the crude product and recrystallization afforded 3.6 gm of the target compound as pale yellow scales (yield: 63%).

Melting Point: 122.5°–123.0° C.

IR($\gamma_{KBr}$, cm$^{-1}$): 2920, 2854, 1617, 1473, 1293, 1155, 786.

$^1$H-NMR(CDCl$_3$, δ): 1.90(6 H, t), 1.12–1.43(20 H, m), 1.56(4 H, bs), 1.60–1.80(4 H, m), 2.47(4 H, t), 6.20(2 H, s), 7.95(4 H, s), 14.6(2 H, bs).

Example 10

Synthesis of 1,3,5-tris(4,4-dimethyl-3-oxopentanoyl)benzene

In a 100 ml three-necked flask equipped with a mechanical stirrer, dropping funnel, reflux condenser, and a nitrogen-inlet tube, 2.29 gm (57 mmol) of 60% sodium hydride, 5.24 gm (52 mmol) of pinacolone, 4.0 gm (15.8 mmol) of trimethyl-1,3,5-benzenetricarboxylate, and 40 ml of anhydrous tetrahydrofuran were mixed with stirring under nitrogen stream, and the refluxing under heat was continued for 7 hours. After cooling the reaction mixture, 30 ml of 2N aqueous hydrochloric acid was added, and the mixture was extracted with chloroform. The extract was dried over anhydrous sodium sulfate and the solvent was removed by evaporation to give a crude product. Acetone was added to the crude product, and recrystallization afforded 3.8 gm of the target compound as yellow crystals (yield: 52%).

$^1$H-NMR(CDCl$_3$, δ): 1.30(27 H, s), 6.41(3 H, s), 8.49(3 H, s), 15.6(3 H, bs).

Example 11

Synthesis of 1,4-bis(4-hydroxy-4-methyl-3-oxopentanoyl)benzene

In a 200 ml three-necked flask equipped with a mechanical stirrer, dropping funnel, reflux condenser, and a nitrogen-inlet tube, 15 gm (147 mmol) of 3-methyl-3-hydroxy-2-butanone, 500 mg (2.0 mmol) of pyridinium p-toluenesulfonate and 100 ml of anhydrous methylene chloride were mixed with stirring under nitrogen stream, and 11.7 gm (162 mmol) of ethylvinylether was added dropwise at room temperature for 3 hours while stirring. After the reaction, the reaction mixture was washed with 5% aqueous sodium hydrogencarbonate, and then the mixture was extracted with chloroform. The extract was dried over anhydrous sodium sulfate and the solvent was removed by evaporation to give a crude product. Distillation of the crude product afforded 17.09 gm of 3-(1-ethoxyethoxy)-3-methyl-butane-2-one (b.p. 38–40/1 mmHg, yield: 66%).

In a 100 ml three-necked flask equipped with a mechanical stirrer, dropping funnel, reflux condenser, and a nitrogen-inlet tube, 9.9 gm (57 mmol) of above-mentioned 3-(1-ethoxyethoxy)-3-methyl-butane-2-one, 2.3 gm (57 mmol) of 60% sodium hydride, 5.0 gm (25 mmol) of dimethylterephthalate and 50 ml of anhydrous tetrahydrofuran were mixed with stirring under nitrogen stream, and the refluxing under heat was continued for 7 hours. After cooling the reaction mixture, 30 ml of 2N hydrochloric acid was added and the mixture was extracted with chloroform. The extract was dried over anhydrous sodium sulfate and the solvent was removed by evaporation. The reaction mixture was stirred at room temperature while adding 30 ml of methnol with ten drops of 2N hydrochloric acid. A mixed solvent of acetone-chloroform was added to the crude product, and recrystallization afforded 4.1 gm of the targe compound as pale yellow crystals (yield: 48%).

Melting Point: 276.5°–277.5° C.

IR($\gamma_{KBr}$, cm$^{-1}$): 3112, 2980, 1690, 1583, 1425, 1356, 1173, 1056, 825.

$^1$H-NMR(CDCl$_3$, δ): 1.52(12 H, s), 6.09(2 H, s), 7.95(4 H, s), 14.8(2 H, bs).

Example 12

Synthesis of 1,4-bis(4-methyl-3-oxo-4-azapentanoyl)benzene

In a 200 ml three-necked flask equipped with a mechanical stirrer, dropping funnel, reflux condenser, and a nitrogen-inlet tube, 5.0 gm (125 mmol) of 60% sodium hydride, 10.6 gm (122 mmol) of dimethylacetoamide, 10 gm (51 mmol) of dimethylterephthalate and 100 ml of anhydrous tetrahydrofuran were mixed with stirring under nitrogen stream, and the refluxing under heat was continued for 4 hours. After cooling the reaction mixture, 65 ml of 2N aqueous hydrochloric acid was added and the mixture was extracted with chloroform. The extract was dried over anhydrous sodium sulfate and the solvent was removed by evaporation to give a crude product. A mixed solvent of chloroform-ethanol was added to the crude product, and recrystallization afforded 10.0 gm of the target compound as yellow crystals (yield: 64%).

Melting Point: 188.0°–189.0° C.

IR($\gamma_{KBr}$, cm$^{-1}$): 2932, 1620, 1500, 1440, 1360, 1125, 786, 640.

$^1$H-NMR(CDCl$_3$, δ): 3.10(12 H, s), 4.13(0.4 H, s), 5.88(1.6 H, s), 7.82(3.2 H, s), 7.75(0.4 H, d), 8.05(0.4 H, d).

Example 13

Synthesis of 1-(4-methyl-3-oxo-4-azapentanoyl)-4-(4,4-dimethyl-3-oxopentanoyl)benzene In a 100 ml three-necked flask equipped with a mechanical stirrer, dropping funnel, reflux condenser, and a nitrogen-inlet tube, 5.0 gm (125 mmol) of 60% sodium hydride, 5.1 gm (51 mmol) of pinacolone, 10 gm (51 mmol) of dimethylterephthalate, and 30 ml of anhydrous tetrahydrofuran were mixed with stirring under nitrogen stream, and the refluxing under heat was continued for 4 hours. The refluxing under heat was kept for another 3 hours while adding dropwise 4.4 gm (51 mmol) of dimethyl acetoamide. After cooling the the reaction mixture, 65 ml of 2N aqueous hydrochloric acid was added, and the mixture was extracted with chloroform. The extract was dried over anhydrous sodium sulfate and the solvent was removed by evaporation to give a crude product. Acetone was added to the crude product, and recrystallization afforded 6.9 gm of the target compound as pale yellow crystals (yield: 43%).

Melting Point: 158.7°–160.1° C.

IR($\gamma_{KBr}$, cm$^{-1}$): 3010, 1610, 1503, 1368, 1290, 1164, 1116.

$^1$H-NMR(CDCl$_3$, δ): 1.29(9 H, s), 3.10(6 H, bs), 4.15(0.3 H, s), 5.88(0.7 H, s), 6.35(1 H, s), 7.78–8.10(4 H, m).

Experimental Example 1

UV-Ray Absorbing Effect of the Compounds of the Present Invention

The absorbance as the UV-ray absorbing effect was measured on the Invention Compounds (Ia)–(Ie) prepared in Examples 1–4 and 6, Invention Compound (If)–(Il) prepared in Examples 7–13, and Comparative Compounds shown below according to the method described below. The results are shown in Table 1.

Invention Compound:
- (Ia): 3,4-dimethoxy(4,4-dimethyl-3-oxopentanoyl)benzene
- (Ib): 3,4,5-trimethoxy(4-4-dimethyl-3-oxopentanoyl)benzene
- (Ic): 1,4-bis(4,4-dimethyl-3-oxopentanoyl)benzene
- (Id): 1,3-bis(4,4-dimethyl-3-oxopentanoyl)benzene
- (Ie): 2,6-bis(4,4-dimethyl-3-oxopentanoyl) naphthalene
- (If): 1,4-bis(4-methyl-3-oxopentanoyl)benzene
- (Ig): 1,4-bis(3-oxopentanoyl)benzene
- (Ih): 1,4-bis(3-oxododecanoyl)benzene
- (Ii): 1,3,5-tris(4,4-dimethyl-3-oxopentanoyl)benzene
- (Ij): 1,4-bis(4-hydroxy-4-methyl-3-oxopentanoyl)benzene
- (Ik): 1,4-bis(4-methyl-3-oxo-4-azapentanoyl)benzene
- (Il): 1-(4-methyl-3-oxo-4-azapentanoyl)-4-(4,4-dimethyl-3-oxopentanoyl)benzene Comparative Compound:
1. 2-hydroxy-4-methoxybenzophenone (commercial UV-A absorber)
2. 2-ethylhexyl p-methoxycinnamate (commercial UV-B absorber)

Measuring Method

Ethanol solutions of each Invention Compound and Comparative Compound were prepared (concentration: $2.5 \times 10^{-5}$ mol/l, ethanol: 99.5% reagent, Special grade). Each solution was injected in a quartz cell (1 cm × 1 cm) and its absorbance was measured using an automatic recording spectrophotometer (U-3410 model; manufactured by Hitachi, Ltd.).

TABLE 1

| | (UV-ray absorbing effect) | | | | | | | | | | | | | |
|---|---|---|---|---|---|---|---|---|---|---|---|---|---|---|
| Wavelength | Invention Compound | | | | | | | | | | | | Comparative Compound | |
| (nm) | Ia | Ib | Ic | Id | Ie | If | Ig | Ih | Ii | Ij | Ik | Il | 1 | 2 |
| 290 | 0.24 | 0.25 | 0.27 | 0.54 | 0.44 | 0.23 | 0.23 | 0.24 | 0.51 | 0.28 | 0.28 | 0.26 | 0.40 | 0.54 |
| 300 | 0.29 | 0.36 | 0.38 | 0.74 | 0.29 | 0.34 | 0.34 | 0.34 | 0.71 | 0.41 | 0.37 | 0.36 | 0.28 | 0.60 |
| 310 | 0.37 | 0.46 | 0.49 | 0.85 | 0.43 | 0.45 | 0.43 | 0.44 | 0.87 | 0.60 | 0.49 | 0.47 | 0.24 | 0.64 |
| 320 | 0.49 | 0.52 | 0.62 | 0.84 | 0.55 | 0.57 | 0.54 | 0.59 | 0.89 | 0.78 | 0.57 | 0.56 | 0.25 | 0.52 |
| 330 | 0.57 | 0.51 | 0.78 | 0.70 | 0.75 | 0.71 | 0.66 | 0.75 | 0.75 | 0.98 | 0.61 | 0.65 | 0.25 | 0.27 |
| 340 | 0.55 | 0.43 | 0.87 | 0.44 | 0.91 | 0.81 | 0.75 | 0.85 | 0.56 | 0.99 | 0.57 | 0.66 | 0.21 | 0.08 |
| 350 | 0.38 | 0.24 | 0.83 | 0.21 | 0.97 | 0.79 | 0.73 | 0.84 | 0.30 | 0.98 | 0.45 | 0.59 | 0.13 | 0.02 |
| 360 | 0.21 | 0.13 | 0.68 | 0.05 | 0.88 | 0.67 | 0.64 | 0.71 | 0.12 | 0.61 | 0.29 | 0.44 | 0.06 | 0.01 |
| 370 | 0.06 | 0.03 | 0.40 | 0.01 | 0.73 | 0.45 | 0.45 | 0.46 | 0.01 | 0.45 | 0.15 | 0.28 | 0.03 | 0 |
| 380 | 0.01 | 0.01 | 0.20 | 0 | 0.55 | 0.26 | 0.31 | 0.26 | 0 | 0.08 | 0.05 | 0.13 | 0.01 | 0 |
| 390 | 0 | 0 | 0.30 | 0 | 0.26 | 0.06 | 0.16 | 0.06 | 0 | 0.02 | 0.01 | 0.03 | 0 | 0 |
| 400 | 0 | 0 | 0.01 | 0 | 0.09 | 0.02 | 0.10 | 0.01 | 0 | 0.01 | 0 | 0.01 | 0 | 0 |

As clearly shown in Table 1, the compounds of the present invention possess UV-A and UV-B absorbing effects higher than conventional compounds, 2-hydroxy-4-methoxybenzophenone and 2-ethylhexyl-p-methoxycinnamate. This is the evidence that the compounds of the present invention exhibit a superior sunscreening effect.

Experimental Example 2

Stability of the Compound of the Present Invention Against UV-Rays

Experiment Procedure

Each of the Invention Compounds or the Comparative Compounds was dissolved in a 99.5% ethanol/distilled water (3/2) solvent to prepare 2 mmol/l concentration solutions. Onto the solution UV-ray was irradiated for 14 hours using a xenon fading tester having a similar wave length and strength as those of sun light. After the solvent was evaporated, each sample was subjected to quantitative analysis for measuring the residual rate of the composition to determine the stability against light of each composition. The results are shown in Table 2.

TABLE 2

(Stability against light)

| Compound | Residual rate (%) Hours after start of irradiation | |
|---|---|---|
| | 14 hours | 65 hours |
| Invention Composition | | |
| Ia | >99 | 99 |
| Ib | >99 | 99 |
| Ic | 99 | 96 |
| Id | 99 | 95 |
| Ie | 99 | 95 |
| If | 99 | 94 |
| Ig | 99 | 94 |
| Ih | 99 | 95 |
| Ii | 99 | 96 |
| Ij | 99 | 95 |
| Ik | 97 | 92 |
| Il | 96 | 92 |
| Comparative Composition | | |
| 2 | 42 | 10 |
| 3* | 73 | 29 |

*Comparative Composition 3: 4-methoxy-4'-t-butyl-benzoylmethane

From the results in Table 2, the compounds of the present invention apparently have an outstanding stability against UV-rays in comparison with 4-methoxy-4'-t-butyldibenzoyl-methane and 2-ethylhexyl-p-methoxycinnamate which are known as a general UV-A absorbing agent and UV-B absorbing agent respectively.

Example 14

O/W cream

The following components were formulated according to a known method to prepare O/W creams.

| <Formulation> | Wt % |
|---|---|
| Invention Compounds (Ia)–(Il) | 2.0 |
| Stearic acid | 1.0 |
| Lipophilic-type monostearic acid glyceride | 2.0 |
| Polyoxyethylenesorbitane monostearate | 1.0 |
| Cetyl alcohol | 1.0 |
| Stearyl alcohol | 1.0 |
| Squalane | 10.0 |
| Liquid paraffin | 20.0 |
| Vaseline | 5.0 |
| Butyl parabene | 0.1 |
| Methyl parabene | 0.1 |
| Triethanol amine | 1.0 |
| Glycerol | 10.0 |
| Perfume | q.s. |
| Water | Balance |
| Total | 100.0 |

Example 15

W/O cream

The following components were formulated according to a known method to prepare W/O creams.

| <Formulation> | Wt % |
|---|---|
| Invention Compounds (Ia)–(Il) | 2.0 |
| Sorbitan sesquioleate | 4.0 |
| Aluminum stearate | 0.5 |
| Cetyl alcohol | 4.0 |
| Liquid paraffin | 16.0 |
| Squalane | 10.0 |
| Isopropylmyristate | 5.0 |
| Sodium benzoate | 0.3 |
| Glycerol | 10.0 |
| Perfume | q.s. |
| Water | Balance |
| Total | 100.0 |

Example 16

O/W Milky Lotion

The following components were formulated according to a known method to prepare O/W milky lotions.

| <Formulation> | Wt % |
|---|---|
| Invention Compounds (Ia)–(Il) | 3.0 |
| Stearic acid | 2.0 |
| Sorbitan monostearate | 1.5 |
| Polyoxyethylenesorbitane monostearate | 1.0 |
| Cetyl alcohol | 0.4 |
| Stearyl alcohol | 0.3 |
| Isopropylmyristate | 7.0 |
| Squalane | 5.0 |
| Liquid paraffin | 5.0 |
| Solid paraffin | 2.0 |
| Ethyl parabene | 0.1 |
| Methyl parabene | 0.1 |
| Carbopole | 0.2 |
| Potassium hydroxide | 0.4 |
| Perfume | q.s. |
| Water | Balance |
| Total | 100.0 |

Example 17

Toilet Lotion

The following components were formulated according to a known method to prepare toilet lotions.

| <Formulation> | Wt % |
|---|---|
| Invention Compound (Ia)–(Il) | 2.0 |
| Polyoxyethylene (23 EO) laurylether | 4.0 |
| Ethanol | 10.0 |
| Glycerol | 3.0 |
| Dipropylene glycol | 7.0 |
| Lactic acid | 0.05 |
| Sodium lactate | 0.12 |
| Methyl parabene | 0.1 |
| Perfume | q.s. |
| Pigment | Small amount |
| Water | Balance |
| Total | 100.0 |

The aroyl ketone derivative (I) of the present invention can provide an excellent UV-ray absorbing effect and has an outstanding stability against light. Thus the UV-ray absorber or cosmetic composition containing the aroyl ketone derivative (I) can exhibit an excellent sunscreening effect.

What is claimed is:

1. An aroyl ketone derivative represented by formula (I):

$$Ar(COCH_2COR^1)_n \qquad (I)$$

wherein $R^1$ is tertiary butyl or n-heptyl; n is 1, 2 or 3; and Ar is a di- or tri-methoxy substituted benzene ring.

2. The aroyl ketone derivative of claim 1, wherein $R^1$ is tertiary butyl; n is 1; and Ar is a di-methoxy substituted benzene ring.

3. The aroyl ketone derivative of claim 1, wherein $R^1$ is tertiary butyl; n is 1; and Ar is a tri-methoxy substituted benzene ring.